United States Patent
Long et al.

(10) Patent No.: US 8,353,848 B2
(45) Date of Patent: Jan. 15, 2013

(54) TEST DEVICE

(75) Inventors: Nicholas Long, Hampton (GB); Jon Johnson, Cambridge (GB)

(73) Assignee: Alere Switzerland GmbH, Zug (CH)

( * ) Notice: Subject to any disclaimer, the term of this patent is extended or adjusted under 35 U.S.C. 154(b) by 763 days.

(21) Appl. No.: 12/094,496

(22) PCT Filed: Nov. 21, 2006

(86) PCT No.: PCT/GB2006/004336
§ 371 (c)(1), (2), (4) Date: Nov. 6, 2008

(87) PCT Pub. No.: WO2007/057704
PCT Pub. Date: May 24, 2007

(65) Prior Publication Data
US 2009/0216155 A1  Aug. 27, 2009

Related U.S. Application Data

(60) Provisional application No. 60/765,246, filed on Feb. 3, 2006.

(30) Foreign Application Priority Data

Nov. 21, 2005 (GB) .................................. 0523663.3

(51) Int. Cl.
*A61B 5/151* (2006.01)
(52) U.S. Cl. ........................ 600/573; 600/583
(58) Field of Classification Search .................. 600/583, 600/573; 606/181–183
See application file for complete search history.

(56) References Cited

U.S. PATENT DOCUMENTS

| | | | |
|---|---|---|---|
| 6,168,606 B1 * | 1/2001 | Levin et al. | 606/181 |
| 6,331,715 B1 * | 12/2001 | Mauchan et al. | 250/559.4 |
| 6,582,964 B1 | 6/2003 | Samsoondar et al. | |
| 6,730,494 B1 * | 5/2004 | Toranto et al. | 435/28 |
| 6,837,858 B2 * | 1/2005 | Cunningham et al. | 600/573 |
| 7,223,248 B2 * | 5/2007 | Erickson et al. | 600/584 |
| 7,766,845 B2 * | 8/2010 | Thym et al. | 600/583 |
| 7,883,473 B2 * | 2/2011 | LeVaughn et al. | 600/583 |
| 8,202,488 B2 * | 6/2012 | Jung et al. | 422/402 |
| 2002/0169393 A1 * | 11/2002 | Cunningham et al. | 600/573 |

(Continued)

FOREIGN PATENT DOCUMENTS

EP  1 167 538  1/2002

(Continued)

OTHER PUBLICATIONS

International Searching Authority from PCT/GB2006/004336.

(Continued)

*Primary Examiner* — Sean P Dougherty
*Assistant Examiner* — Michael C Stout
(74) *Attorney, Agent, or Firm* — Foley Hoag LLP

(57) ABSTRACT

A disposable test device consists of a first portion 2 having a fluid application port 5 to which a sample of fluid can be applied, and a handle portion 3 hingedly attached to the first portion 2 at a hinge portion 4 and which normally lies in the plane of the first portion. In use the device is held by the handle portion 3 and the first portion inserted into a measuring instrument. The handle is then deflected downwardly e.g. by the finger of a person to supply a drop of fluid to the port 5.

16 Claims, 4 Drawing Sheets

U.S. PATENT DOCUMENTS

| | | | |
|---|---|---|---|
| 2003/0143113 A2 * | 7/2003 | Yuzhakov et al. | 422/56 |
| 2003/0144608 A1 * | 7/2003 | Kojima et al. | 600/583 |
| 2003/0223906 A1 * | 12/2003 | McAllister et al. | 422/58 |
| 2004/0122323 A1 * | 6/2004 | Vortman et al. | 600/459 |
| 2004/0127818 A1 * | 7/2004 | Roe et al. | 600/583 |
| 2004/0138588 A1 * | 7/2004 | Saikley et al. | 600/583 |
| 2004/0186394 A1 * | 9/2004 | Roe et al. | 600/583 |
| 2005/0036909 A1 * | 2/2005 | Erickson et al. | 422/61 |
| 2005/0153457 A1 * | 7/2005 | Patel et al. | 436/169 |
| 2005/0240119 A1 * | 10/2005 | Draudt et al. | 600/583 |
| 2005/0284773 A1 * | 12/2005 | Allen | 205/777.5 |
| 2006/0200045 A1 * | 9/2006 | Roe | 600/583 |
| 2006/0247555 A1 * | 11/2006 | Harttig | 600/584 |
| 2011/0009774 A1 * | 1/2011 | Calasso et al. | 600/583 |
| 2011/0009892 A1 * | 1/2011 | Schoenberg | 606/181 |

FOREIGN PATENT DOCUMENTS

| | | |
|---|---|---|
| EP | 1 508 304 | 10/2006 |
| EP | 1 714 613 | 10/2006 |
| WO | WO-2005/112742 | 12/2005 |
| WO | WO 2005112742 A2 * | 12/2005 |

OTHER PUBLICATIONS http://www.medizin-forum.de/herzklappen/quick1.htm (Feb. 11, 2005). Accessed from http://web.archive.org Aug. 25, 2008.

* cited by examiner

TEST DEVICE

RELATED APPLICATIONS

This application claims priority to PCT Application No. PCT/GB06/004336, filed Nov. 21, 2006, which claims the benefit of United Kingdom application no. GB 0523663.3, filed 21 Nov. 2005 and U.S. application No. 60/765,246, filed 3 Feb. 2006. These applications are incorporated herein by reference in their entireties.

This invention relates to analysis of samples and test devices therefor. It particularly relates to test devices and methods for diagnosing samples of fluids. It more particularly relates to devices and methods for diagnosing blood samples.

Disposable diagnostic test devices designed for insertion into a reader in order to measure the presence or amount of an analyte in a fluid sample or property thereof are well known. Such tests are used routinely, such as for example the measurement of blood glucose, or the measurement of prothrombin time.

The user is typically required insert a test device in the reader and then apply a small sample of bodily fluid (of the order of 1-10 μL) to be tested to the test device. The sample fluid is typically drawn into the interior of the test device along a capillary channel via a sample inlet port. The bodily fluid may for example be blood obtained using a finger stick from a convenient sampling point such as a finger.

After the test has been completed, the test device may be removed from the reader and discarded. In view of relatively small size of the device, some users can find it quite difficult to remove it from the reader. Generally the test device is designed to engage firmly with the reader such that the test device is not dislodged during measurement. However, this can present difficulties for some users in manually removing and inserting the test device from the reader, as a degree of effort may be required. The size of the test device only serves to exacerbate the issue.

Due to the fact that the used device has been contaminated with sample and in view of its relatively small size (which in an exemplary known type is 2 cm in length×0.5 cm in width), many readers are provided with a device ejection means. This removes the need for the user to manually remove the device as well as reducing the chances of contamination of the user by the soiled device. However it is not always practical to provide an ejection means in some cases manual removal of the device may be a preferred option.

A convenient way of applying sample to the test device is by end-fill. The user merely has to contact the end of the device with the fluid sample in order to supply fluid sample to the device, for example by contacting the device with a finger. However, provision of a fluid sample region at the end of the device makes it more difficult to remove after use without contaminating the user.

The present invention seeks to provide an improved test device.

One aspect of the invention provides a test device for applying samples to be tested to a test reader, comprising a first portion (2), having a sample port (5) arranged to receive a fluid sample to be tested, and a second portion (3) comprising grip means arranged to facilitate manual handing by a user deflectably coupled to the first portion at a hinge portion (4).

In some embodiments, the second portion comprises a generally U shaped frame. In further embodiments, the frame in the undeflected state surrounds the sample port.

In some embodiments, the sample port is arranged at an end of the first portion. In further embodiments, the sample port is arranged at the end of the first portion which is coupled to the second portion at the hinge portion.

In some embodiments, the hinge portion comprises resilient means arranged to bias the first and second portions to a predetermined alignment.

In some embodiments, the first portion (2), second portion (3) and hinge portion (4) are a unitary body, the hinge portion (4) being constituted by a deformable portion. In further embodiments, the hinge portion is thinner than the first and second portions.

In some embodiments, at least the hinge portion is of laminated construction. In further embodiments, the hinge is constituted by providing a groove extending at least partially through at least one layer of the laminated construction.

In some embodiments, the first and second portions are discrete members pivotably coupled together at the hinge portion.

Another aspect of the invention provides a device, comprising:
a first portion comprising a capillary opening, a capillary, and a detection zone connected to the capillary opening by the capillary, the first portion defining a major axis extending between first and second ends of the first portion, the capillary opening being proximate the first end of the first portion, a second portion extending beyond the first portion along the major axis and comprising a manipulatable surface and being rotatably connected to the first portion at a bendable portion of the device.

In some embodiments, the detection zone comprises reagents to perform an analysis of a sample applied to the capillary opening. In further embodiments, the reagents are selected to perform a determination of a coagulation time of blood applied to the capillary opening.

In some embodiments, the second portion is rotatable with respect to the first portion about a deflection axis extending generally perpendicular to the major axis of the first portion of the device. In further embodiments, the deflection axis is located between the first and second ends of the first portion of the device. In further embodiments, the deflection axis is located at least 2.5 mm from the first end of the first portion of the device as measured along the major axis. In further embodiments, the deflection axis is located at least 4 mm from the first end of the first portion of the device as measured along the major axis. In other embodiments, the capillary opening is located between the deflection axis and the first end of the first portion as measured along the major axis. In further embodiments, the capillary opening is located at least 1 mm from the first end of the first portion as measured along the major axis.

In some embodiments, the bendable portion has a greater susceptibility to bending than adjacent portions of the device.

In some embodiments, a distance between the capillary opening and an opposite terminal end of the second portion of the device is at least about 1 cm. In further embodiments, the distance is at least about 1.5 cm. In further embodiments, the second portion of the device comprises at least one manipulable surface having an area of at least about 0.6 $cm^2$. In further embodiments, the surface has an area of at least about 1 $cm^2$. In further embodiments, the surface has an area of at least about 1.25 $cm^2$.

One aspect of the invention provides a diagnostic test device for applying samples to be tested to a test reader comprising a first portion having a sample port arranged to receive a fluid sample to be tested, a second portion deflectably coupled to the first portion at a hingeable portion.

In one aspect, the invention relates to a method including inserting an insertion portion of a first portion of a device into a test reader, applying a sample to a sample application zone of the device, and removing the device from the test reader by manipulating a second portion of the device, the sample application zone being located between the first and second portions of the device.

The method may further include performing at least one analysis on the sample applied to the device. The analysis is typically performed prior to removing the device from the test reader. The analysis may include, for example, determining one or more analytes within the sample and/or a determination of a physiochemical property of the sample. In an exemplary embodiment, the sample includes blood and the analysis includes a determination of a coagulation time of blood applied to the device.

In some embodiments, the sample includes blood and the step of applying the sample includes contacting the blood to the sample application zone. The applying can include contacting blood present on a digit of a hand of a human to the sample application zone. The blood may result from, for example, a finger stick to the digit.

The step of applying the sample to the device can be performed before or after the step of inserting the insertion portion. In an exemplary embodiment, the step of applying is performed after the step of inserting and before the step of removing.

In some embodiments, the sample application zone is a capillary opening. The capillary opening may be connected to one or more detection zones (e.g., detection chambers) located within the insertion portion of the first portion of the device. The capillary opening and one or more detection zones may be connected by a capillary. The capillary may have a length of at least about 5 mm (e.g., at least about 8 mm, at least about 10 mm). In an exemplary embodiment, the capillary opening is connected to each of two detection chambers located within the insertion portion of the device and the capillary is between about 8 and 15 mm long.

The method can further include deflecting the second portion of the device through an angle with respect to the first portion of the device. In an exemplary embodiment, the step of deflecting is performed concurrently with and/or prior to the step of applying the sample. In such embodiments, the sample is typically blood present on a digit of a hand (e.g., from a finger stick) which is contacted with the sample application zone. In the undeflected state (e.g., prior to performing the step of deflecting), the second portion of the device may restrict access of a digit of a human hand to the sample application zone (e.g., capillary opening) and in the deflected state (e.g., subsequent to performing the step of deflecting) the sample application permits access of the digit to the sample application zone. Typically, the device is in the undeflected state during at least a portion (e.g., all) of the step of inserting. The device may be in the undeflected state during at least a portion (e.g., all) of the step of removing.

The step deflecting can be performed while at least some of the insertion portion of the first portion remains inserted in the test reader. For example, deflecting the second portion of the device can be performed so while at least about 50% (e.g., at least about 75%, 100%) of an inserted length of the insertion portion remains inserted in the test reader. Deflecting the second portion of the device can be performed before removing more than about 5% (e.g., before removing more than about 2.5%, before removing any) of the inserted length of the insertion portion.

The angle of deflection may be at least about 15 degrees (e.g., at least about 30 degrees) with respect to a major axis of the first portion of the device.

The deflecting can be performed by contacting the second portion of the device with at least first and second digits of a hand of a human (e.g., by grasping the second portion between the thumb and index finger of the hand).

The deflecting can be performed by rotating the second portion about an axis (a) extending generally perpendicular to a major axis of the first portion of the device and (b) generally aligned with or adjacent to the sample application zone of the device.

In some embodiments, the first portion of the device defines a major axis extending between first and second ends of the first portion, the sample application zone is proximate the first end of the first portion of the device, the step of inserting comprises inserting the second end of the first portion into the test reader, and the deflecting is about an deflection axis (a) extending generally perpendicular to the major axis of the first portion of the device and (b) located between the first and second ends of the first portion of the device. The deflection axis may be located at least 2 mm (e.g., at least 2.5, at least 4 mm) from the first end of the first portion of the device as measured along the major axis.

In some embodiments, the sample application zone is a capillary opening located between the deflection axis and the first end of the first portion. The capillary opening may be located at least 0.75 mm (e.g., at least 1 mm, at least 1.5 mm) from the first end of the first portion as measured along the major axis.

The deflecting may be about an axis generally defined by a bendable portion of the device, the deflectable portion having a greater susceptibility to bending than adjacent portions of the device.

The step of manipulating can be performed by contacting the second portion of the device with at least first and second digits of a hand of a human (e.g., by grasping the second portion between the thumb and index finger of the hand). The manipulating may comprise a pulling motion directed generally along a major axis of the first portion of the device and away from the test reader.

A distance between the sample application zone and an opposite terminal end of the second portion of the device may be sufficient that the manipulating is performed without the first and second digits contacting sample remaining at the sample application zone. For example, a distance between the sample application zone and an opposite terminal end of the second portion of the device may be at least about 1 cm (e.g., at least about 1.5 cm).

A perimeter of second portion of the device may enclose an area of at least about 0.6 cm$^2$ (e.g., at least about 1 cm$^2$, at least about 1.25 cm$^2$, at least about 1.25 cm$^2$). The second portion of the device may include at least one manipulatable surface having an area of at least about 0.6 cm$^2$ (e.g., at least about 1 cm$^2$, at least about 1.25 cm$^2$, at least about 1.25 cm$^2$).

In another aspect, the invention relates to a method including inserting an insertion portion of a first portion of a device into a test reader, deflecting a second portion of the device with respect to the first portion of the device, the sample application zone being located between the first and second portions of the device, and applying a sample to a sample application zone of the device.

The method may further include performing at least one analysis on the sample applied to the device. The analysis is typically performed prior to removing the device from the test reader. The analysis may include, for example, determining one or more analytes within the sample and/or a determination of a physiochemical property of the sample. In an exemplary embodiment, the sample includes blood and the analysis includes a determination of a coagulation time of blood applied to the device.

In some embodiments, the sample includes blood and the step of applying the sample includes contacting the blood to the sample application zone. The applying can include contacting blood present on a digit of a hand of a human to the sample application zone. The blood may result from, for example, a finger stick to the digit.

The step of applying the sample to the device can be performed before or after the step of inserting the insertion portion. In an exemplary embodiment, the step of applying is performed after the step of inserting and before a step of removing the device from the test reader.

In some embodiments, the sample application zone is a capillary opening. The capillary opening may be connected to one or more detection zones (e.g., detection chambers) located within the insertion portion of the first portion of the device. The capillary opening and one or more detection zones may be connected by a capillary. The capillary may have a length of at least about 5 mm (e.g., at least about 8 mm, at least about 10 mm). In an exemplary embodiment, the capillary opening is connected to each of two detection chambers located within the insertion portion of the device and the capillary is between about 8 and 15 mm long.

The deflecting typically includes deflecting the second portion of the device through an angle with respect to the first portion of the device. In an exemplary embodiment, the step of deflecting is performed concurrently with and/or prior to the step of applying the sample. In such embodiments, the sample is typically blood present on a digit of a hand (e.g., from a finger stick) which is contacted with the sample application zone. In the undeflected state (e.g., prior to performing the step of deflecting), the second portion of the device may restrict access of a digit of a human hand to the sample application zone (e.g., capillary opening) and in the deflected state (e.g., subsequent to performing the step of deflecting) the sample application permits access of the digit to the sample application zone. Typically, the device is in the undeflected state during at least a portion (e.g., all) of the step of inserting. The device may be in the undeflected state during at least a portion (e.g., all) of the step of removing.

The step deflecting can be performed while at least some of the insertion portion of the first portion remains inserted in the test reader. For example, deflecting the second portion of the device can be performed so while at least about 50% (e.g., at least about 75%, 100%) of an inserted length of the insertion portion remains inserted in the test reader. Deflecting the second of the device can be performed before removing more than about 5% (e.g., before removing more than about 2.5%, before removing any) of the inserted length of the insertion portion.

The angle of deflection may be at least about 15 degrees (e.g., at least about 30 degrees) with respect to a major axis of the first portion of the device.

The deflecting can be performed by contacting the second portion of the device with at least first and second digits of a hand of a human (e.g., by grasping the second portion between the thumb and index finger of the hand).

The deflecting can be performed by rotating the second portion about an axis (a) extending generally perpendicular to a major axis of the first portion of the device and (b) generally aligned with or adjacent to the sample application zone of the device.

In some embodiments, the first portion of the device defines a major axis extending between first and second ends of the first portion, the sample application zone is proximate the first end of the first portion of the device, the step of inserting comprises inserting the second end of the first portion into the test reader, and the deflecting is about an deflection axis (a) extending generally perpendicular to the major axis of the first portion of the device and (b) located between the first and second ends of the first portion of the device. The deflection axis may be located at least 2 mm (e.g., at least 2.5, at least 4 mm) from the first end of the first portion of the device as measured along the major axis.

In some embodiments, the sample application zone is a capillary opening located between the deflection axis and the first end of the first portion. The capillary opening may be located at least 0.75 mm (e.g., at least 1 mm, at least 1.5 mm) from the first end of the first portion as measured along the major axis.

The deflecting may be about an axis generally defined by a bendable portion of the device, the deflectable portion having a greater susceptibility to bending than adjacent portions of the device.

The step of manipulating can be performed by contacting the second portion of the device with at least first and second digits of a hand of a human (e.g., by grasping the second portion between the thumb and index finger of the hand). The manipulating may comprise a pulling motion directed generally along a major axis of the first portion of the device and away from the test reader.

The distance between the sample application zone and an opposite terminal end of the second portion of the device may be sufficient that the manipulating is performed without the first and second digits contacting sample remaining at the sample application zone. For example, the distance between the sample application zone and an opposite terminal end of the second portion of the device may be at least about 1 cm (e.g., at least about 1.5 cm).

A perimeter of second portion of the device may enclose an area of at least about $0.6\,cm^2$ (e.g., at least about $1\,cm^2$, at least about $1.25\,cm^2$). The second portion of the device may include at least one manipulatable surface having an area of at least about $0.6\,cm^2$ (e.g., at least about $1\,cm^2$, at least about $1.25\,cm^2$).

In another aspect, the invention relates to a method including deflecting a second portion of a device with respect to a first portion of the device, the deflecting exposing to a digit of a human hand a previously obstructed sample application zone of the first portion of the device so that the sample input can receive a fluid sample applied to the sample application zone, the sample input being located between the first and second portions of the device, inserting an insertion portion of a first portion of a device into a test reader, applying a sample to a sample application zone of the device, and removing the device from the test reader by manipulating the second portion of the device.

The method may further include performing at least one analysis on the sample applied to the device. The analysis is typically performed prior to removing the device from the test reader. The analysis may include, for example, determining one or more analytes within the sample and/or a determination of a physiochemical property of the sample. In an exemplary embodiment, the sample includes blood and the analysis includes a determination of a coagulation time of blood applied to the device.

In some embodiments, the sample includes blood and the step of applying the sample includes contacting the blood to the sample application zone. The applying can include contacting blood present on a digit of a hand of a human to the sample application zone. The blood may result from, for example, a finger stick to the digit.

The step of applying the sample to the device can be performed before or after the step of inserting the insertion portion. In an exemplary embodiment, the step of applying is performed after the step of inserting and before the step of removing.

In some embodiments, the sample application zone is a capillary opening. The capillary opening may be connected to one or more detection zones (e.g., detection chambers) located within the insertion portion of the first portion of the device. The capillary opening and one or more detection zones may be connected by a capillary. The capillary may have a length of at least about 5 mm (e.g., at least about 8 mm, or at least about 10 mm). In an exemplary embodiment, the capillary opening is connected to each of two detection chambers located within the insertion portion of the device and the capillary is between about 8 and 15 mm long.

The method can further include deflecting the second portion of the device through an angle with respect to the first portion of the device. In an exemplary embodiment, the step of deflecting is performed concurrently with and/or prior to the step of applying the sample. In such embodiments, the sample is typically blood present on a digit of a hand (e.g., from a finger stick) which is contacted with the sample application zone. In the undeflected state (e.g., prior to performing the step of deflecting), the second portion of the device may restrict access of a digit of a human hand to the sample application zone (e.g., capillary opening) and in the deflected state (e.g., subsequent to performing the step of deflecting) the sample application permits access of the digit to the sample application zone. Typically, the device is in the undeflected state during at least a portion (e.g., all) of the step of inserting. The device may be in the undeflected state during at least a portion (e.g., all) of the step of removing.

The step deflecting can be performed while at least some of the insertion portion of the first portion remains inserted in the test reader. For example, deflecting the second portion of the device can be performed so while at least about 50% (e.g., at least about 75%, or even 100%) of the inserted length of the insertion portion remains inserted in the test reader. Deflecting the second portion of the device can be performed before removing more than about 5% (e.g., before removing more than about 2.5%, or before removing any) of the inserted length of the insertion portion.

The angle of deflection may be at least about 15 degrees (e.g., at least about 30 degrees) with respect to a major axis of the first portion of the device.

The deflecting can be performed by contacting the second portion of the device with at least first and second digits of a hand of a human (e.g., by grasping the second portion between the thumb and index finger of the hand).

The deflecting can be performed by rotating the second portion about an axis (a) extending generally perpendicular to a major axis of the first portion of the device and (b) generally aligned with or adjacent to the sample application zone of the device.

In some embodiments, the first portion of the device defines a major axis extending between first and second ends of the first portion, the sample application zone is proximate the first end of the first portion of the device, the step of inserting comprises inserting the second end of the first portion into the test device, and the deflecting is about an deflection axis (a) extending generally perpendicular to the major axis of the first portion of the device and (b) located between the first and second ends of the first portion of the device. The deflection axis may be located at least 2 mm (e.g., at least 2.5, or at least 4 mm) from the first end of the first portion of the device as measured along the major axis.

In some embodiments, the sample application zone is a capillary opening located between the deflection axis and the first end of the first portion. The capillary opening may be located at least 0.75 mm (e.g., at least 1 mm, or at least 1.5 mm) from the first end of the first portion as measured along the major axis.

The deflecting may be about an axis generally defined by a bendable portion of the device, the deflectable portion having a greater susceptibility to bending than adjacent portions of the device.

The step of manipulating can be performed by contacting the second portion of the device with at least first and second digits of a hand of a human (e.g., by grasping the second portion between the thumb and index finger of the hand). The manipulating may comprise a pulling motion directed generally along a major axis of the first portion of the device and away from the test reader.

A distance between the sample application zone and an opposite terminal end of the second portion of the device may be sufficient that the manipulating is performed without the first and second digits contacting sample remaining at the sample application zone. For example, a distance between the sample application zone and an opposite terminal end of the second portion of the device may be at least about 1 cm (e.g., at least about 1.5 cm).

A perimeter of the second portion of the device may enclose an area of at least about 0.6 cm$^2$ (e.g., at least about 1 cm$^2$, at least about 1.25 cm$^2$). The second portion of the device may include at least one manipulatable surface having an area of at least about 0.6 cm$^2$ (e.g., at least about 1 cm$^2$, at least about 1.25 cm$^2$).

Another aspect of the invention relates to a device including a first portion including a capillary opening, a capillary, and a detection zone connected to the capillary opening by the capillary. The first portion defines a major axis extending between first and second ends of the first portion. The capillary opening is proximate the first end of the first portion. A second portion of the device extends beyond the first portion along the major axis and includes a manipulatable surface and is rotatably connected to the first portion at a bendable portion of the device.

The device (e.g., the detection zone thereof) typically includes reagents to perform an analysis of a sample applied to the capillary opening. In an exemplary embodiment, the reagents are selected to facilitate determination of a coagulation time of blood applied to the capillary opening.

In some embodiments, the second portion is rotatable with respect to the first portion about a deflection axis extending generally perpendicular to the major axis of the first portion of the device. The deflection axis may be located between the first and second ends of the first portion of the device (e.g., at least 2.5 mm (e.g., at least 4 mm) from the first end of the first portion of the device as measured along the major axis). The capillary opening may be located between the deflection axis and the first end of the first portion as measured along the major axis. For example, the capillary opening may be located at least 0.75 mm (e.g., at least 1 mm, or at least 1.5 mm) from the first end of the first portion as measured along the major axis.

The bendable portion typically has a greater susceptibility to bending than adjacent portions of the device.

In some embodiments, a distance between the capillary opening and an opposite terminal end of the second portion of the device is at least about 1 cm (e.g., at least about 1.5 cm). A perimeter of second portion of the device may enclose an area of at least about 0.6 cm$^2$ (e.g., at least about 1 cm$^2$, or at least about 1.25 cm$^2$). The second portion of the device may include at least one manipulatable surface having an area of at least about 0.6 cm² (e.g., at least about 1 cm², or at least about 1.25 cm²).

Embodiments of the present invention can provide a test device for use in a reader which is able to be removed simply and easily from the reader without necessarily the need for an ejection means. The device is able to be removed by hand whilst reducing the risk of contamination.

Embodiments of the invention will now be described by way of non-limiting example only, with reference to the drawings in which FIG. 1 shows a plan view of a test device in accordance with the invention;

Figure 1:
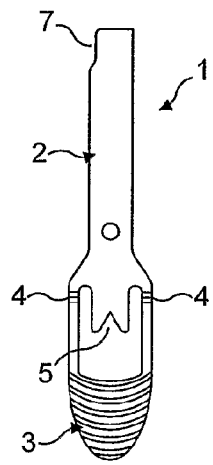

Referring now to FIG. 1, a test device shown generally by 1 consists of a first portion 2 containing a fluidic geometry arrangement and a second portion 3 consisting of a grip which is hingedly connected to the first portion 2 by a hinge portion 4. The first portion 2 has a sample fluid application port 5 for the application of fluids to be tested thereto. As is well known to those skilled in the art, the fluid geometry portion typically includes a capillary which causes fluid applied at an application port to be drawn into a location at which the sample of fluid can be analysed. Details of the fluid geometry portion have not been shown as these are well known to those skilled in the art and are not material to the present invention. An index arrangement 7 ensures that the test device can only be inserted in the correct orientation.

The test device may conveniently be manufactured as a one-piece injection moulding using a single type of plastics material. In this embodiment, polycarbonate (PC) and polyethylene terephalate (PT) have been found to be suitable materials.

Figure 2:
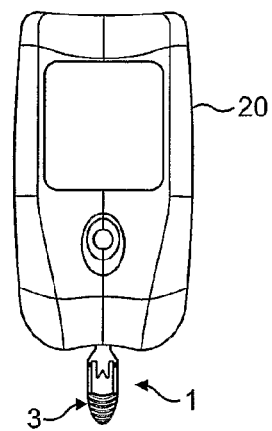
FIG. 2 shows a diagnostic reader with a test device inserted therein.

As shown in FIG. 2, in use the test device 1 is inserted into a reader 20 using the handle 3. It can be seen that the handle 3 allows the user to insert the device into the reader by gripping the grip portion thereof without touching the application port 5.

Figure 3:
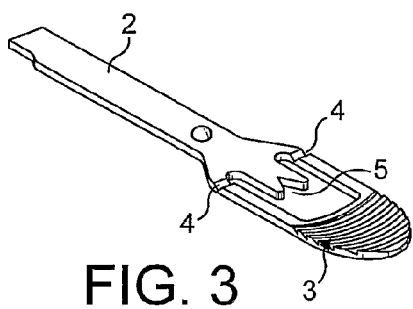
FIG. 3 shows a perspective view of FIG. 1.
Figure 4:
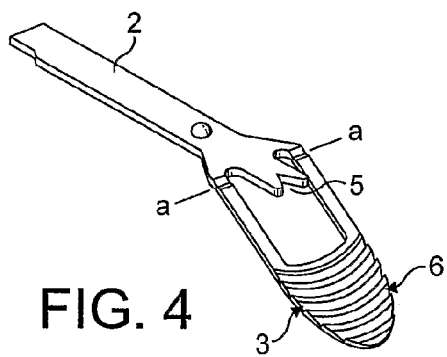
FIG. 4 shows a perspective view of a test device corresponding to FIG. 3 illustrating the mode of use thereof.

As can be seen in FIG. 3, the hinge portion 4 of the present embodiment is formed by making the hinged portion 4 thinner than the portion of the device on either side thereof. As can be seen in FIG. 4, this allows the grip portion 3 to be deflected by hinging about the hinge portion 4 about axis a-a so that it no longer obstructs access to the sample port 5.

The user inserts the test-device 1 into the reader 20 in the conventional fashion holding onto the grip end section 3. The hingeable portion 4 of device 1 is designed such that insertion of the test-device into reader 20 does not cause the end-section 3 to bend significantly. In one mode of use, to apply a sample, the user merely bends the end section 3 downwards and applies the fluid sample through the end-fill sample fluid application port 5. Alternatively, the end-section 3 may be caused to deflect as a consequence of applying the fluid sample to the application port. When the test has been completed, the user can remove the test device 1 by pulling on the end-section 3.

It can be seen that the design allows an end filled test device to be used whilst at the same time allowing the user to easily remove the used test-device from the reader.

In the present embodiment the end-section 3 is provided with a grip means 6 to allow for easy insertion and removal. In this embodiment the grip means comprises a series of arcuate ridges on one surface on the upper surface thereof. As well as providing grip these assist in identifying the correct orientation of the test device for insertion into the reader. However, other forms of grip may be provided on either or both surfaces. In the present embodiment grip 3 is wider than the fluidic geometry portion of the test device to facilitate easy handling due to the physically small size of the fluidic geometry portion of the device. However, this is not essential and other geometries and relative dimensions of the fluidic portion and handle are possible within the scope of the invention.

It can be seen that the end portion protects the sample port whilst not in use. This reduces the likelihood of the fluid sample or any other contaminant such as dirt which might block the fluid channel being introduced inadvertently into the test device during handling. Arrangements in accordance with the invention can also allow a physically larger device to be used in combination with an end-fill without requiring an increase in the internal volume requirements of the fluidic geometry portion of the test device. This can provide an arrangement which is more convenient for the user to handle manually.

The deflectable grip section 3 may also provide a resting place for the finger of the user while a sample is being applied to the sample port. The grip means may provide a tactile indication to the user that his or her finger is in the right place by providing an appropriate configuration of the grip surface. The grip may also serve as a tactile guiding means in order to guide the finger to the device.

The skilled person will appreciate that numerous modifications are possible within the scope of the invention.

For example, the sample port need not be in the location shown in the exemplary embodiment and could for example be located on an upper or lower surface of the device or on one of the lateral sides thereof.

The test device may conveniently be manufactured by injection moulding. The device may also be made by lamination of two or more substrates. Polycarbonate (PC), polypropylene (PP) and polyethylene terephalate (PET) have been found to be suitable materials. The device may be made from a single type of plastics material, or two or more different types may be used. For example, a substrate such as PP may be used at the hinge portion, where its flexible properties can be used with advantage, a relatively less flexible substrate such as PET being used for the remaining portions of the device.

In a further modification, the hinge portion may be thicker than fluidic geometry portion. This allows the provision of a more resilient hinge which offers resistance to deflection and which can allow the grip portion to provide additional support for the finger of a user.

Some exemplary ways of implementing hinge will now be described.

Figure 5:
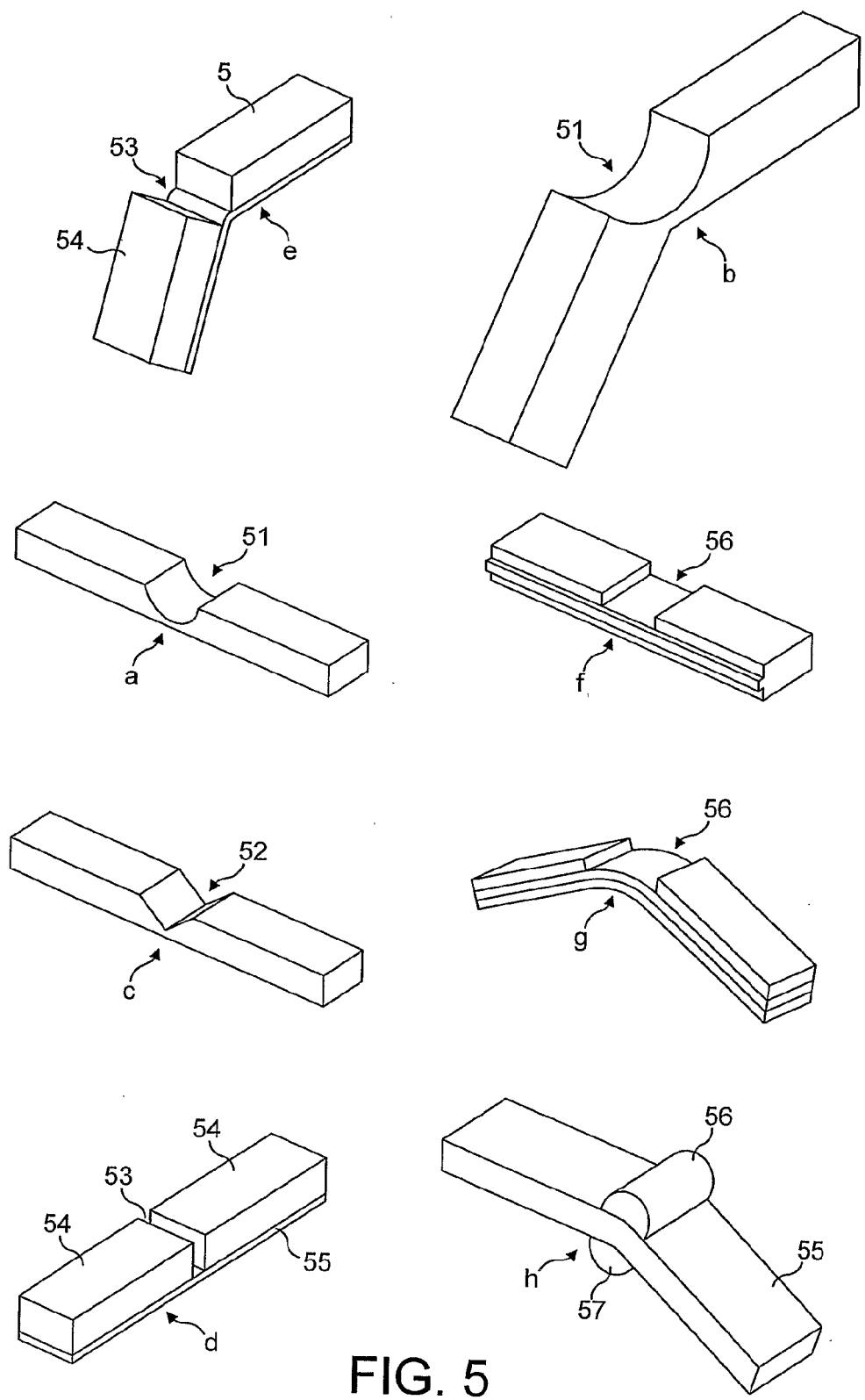
FIG. 5 shows examples of hinge constructions.

FIG. 5a shows a hinge implemented by providing an arcuate transverse groove 51 at the location of the hinge.

FIG. 5b shows the hinge of FIG. 5a in the deflected condition.

FIG. 5c shows a hinge implemented by providing a transverse V groove 52.

FIG. 5d shows a laminated moulded construction where a transverse groove 53 through one layer 54 allows the other layer 55 to function as a hinge. In this embodiment the groove 53 is formed during the moulding operation.

FIG. 5e shows the hinge of FIG. 5d in a deflected state.

FIGS. 5f and 5g show a hinge constructed from a variable laminate profile. A transverse groove 56 is produced by removing material locally e.g. by localised laser cutting.

FIG. 5h illustrates a modification whereby a resilient material 56, 57 is applied at the location of a hinge whose body 55 is formed of relatively less resilient material. The presence of this resilient material 56, 57 causes the hinge to return to a particular position after it has been deflected by a user in use. While the resilient material has been shown applied to both sides of the hinges it will be appreciate that it may only be necessary to apply it on one side. The skilled person will appreciate that resilient material may be applied to the other embodiments of hinges described above.

Test devices in accordance with the invention may be used to test a variety of fluid samples. In particular the fluid sample may be a biological fluid such as blood or interstitial fluid. In addition to sampling fluid from a finger, other parts of the body may be conveniently used such as the side of the palm of the hand.

Figure 6:
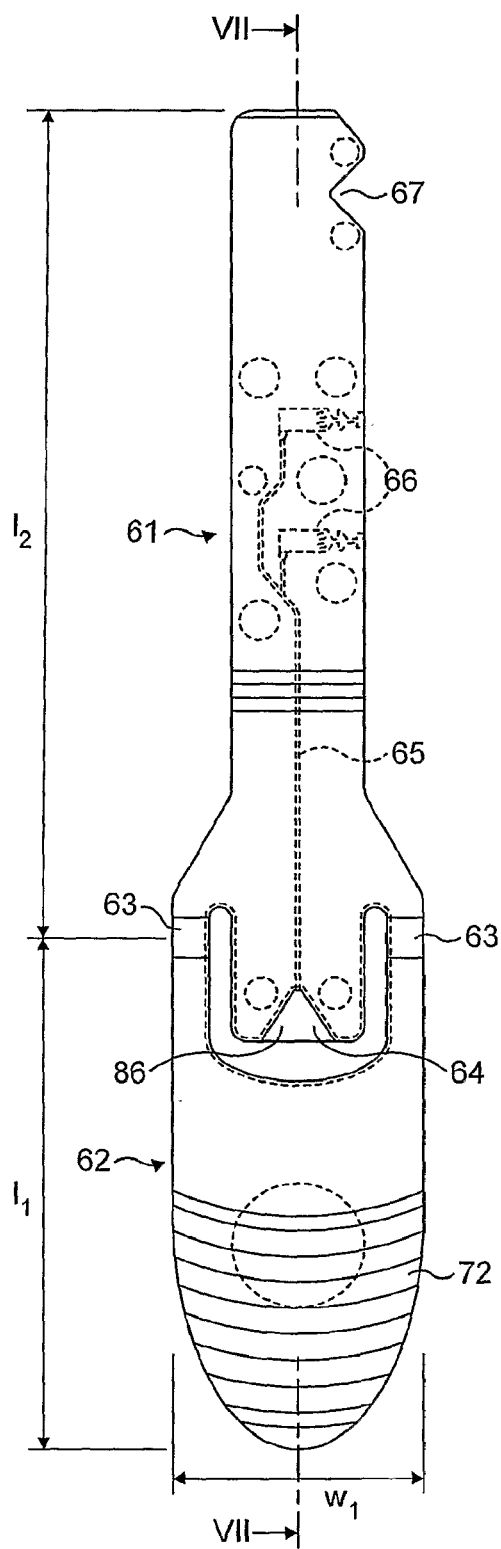
FIG. 6 shows a plan view of another embodiment of the invention.
Figure 7:
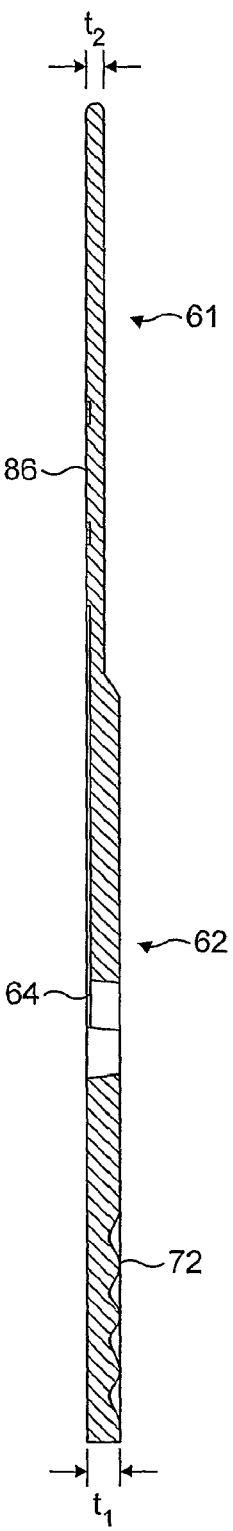
FIG. 7 shows a sectional view of FIG. 6.
Figure 8:
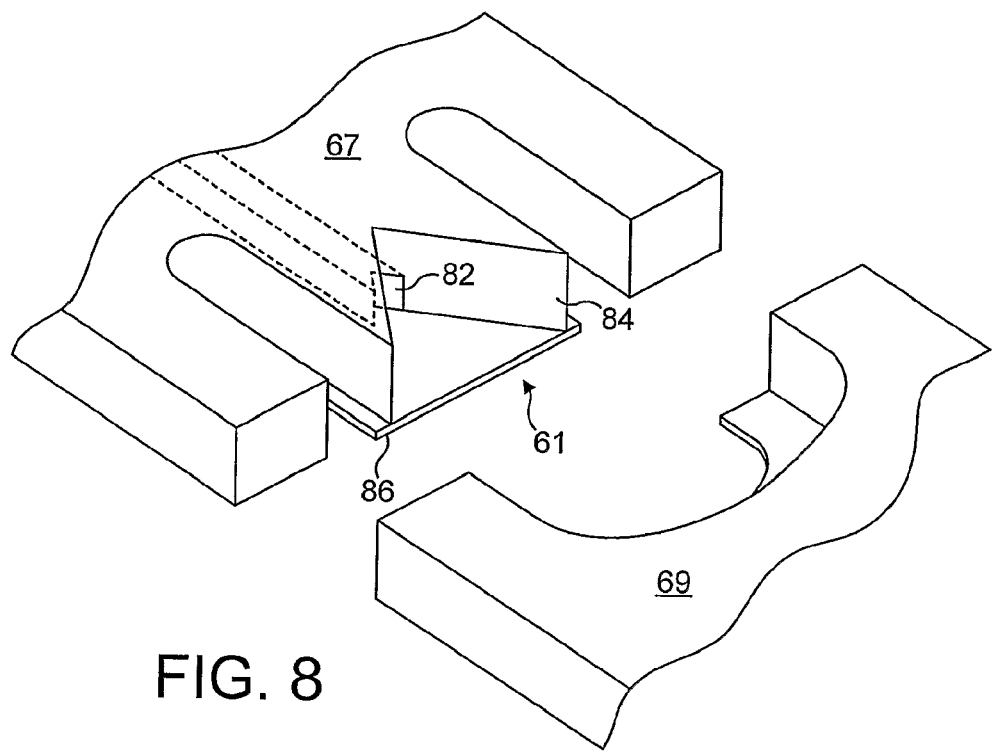
FIG. 8 shows an enlarged perspective view of the sample application zone of the embodiment of FIGS. 6 and 7.

A further embodiment will now be described with reference to FIGS. 6, 7 and 8.

A test device has a first portion 61 and second portion 62 connected together by a hinge portion 63. The first portion has a sample inlet port 64 which communicates with a capillary 65 leading to sample chambers 66 for accommodating samples of a medium to be analysed. A notch 67 provides positive registration of the test device when it is inserted into a test reader or the like as described in connection with FIG. 2 above. The second part 62 functions as a handle as in the previously described embodiment and has an arrangement of ridges of corrugation 72 to facilitate gripping by a user.

In this embodiment the test device is manufactured as a laminated structure consisting of an upper layer and a lower layer. The upper layer has formed therein the capillary 65 and chambers 66 in the form of open channels. These open channels are closed by the application of the lower layer 86 thereto as can be seen more clearly in the enlarged view of FIG. 8. In the present embodiment the handle portion 62 has a length $l_1$ of about 20 mm and a thickness $t_1$ of about 1.3 mm. The test portion has a length $l_2$ measured from the hinge to the end remote from the handle of about 33 mm. Its thickness adjacent the hinge is about 1.3 mm, transitioning to a thickness $t_2$ of 0.7 mm in the portion to be inserted into the measuring instrument. The lower laminate layer has a uniform thickness of about 150 μm. In this embodiment the upper layer is transparent, inter alia to allow the user to visually establish that the sample did reach the sample chambers 66, and the lower layer 86 is a light colour, such as white, to provide a background against which the fluid may be readily seen.

One example of constructing the test device will now be described. The upper portion is constructed as a precision casting, allowing the capillary channels and chambers as well the hinge and grip portions to be formed in a single operation. The lower layer is then attached to the upper layer. For ease of manufacture, in this embodiment the lower layer somewhat overlaps the perimeter of the upper layer and is trimmed to size so as to generally conform to the outline of the upper layer e.g. by laser trimming process. An exception to this is that, as shown in FIG. 8, a portion of the lower layer is intentionally left untrimmed in the vicinity of the sample port 82 so as to produce a funnel-like structure which facilitates the application of a sample to the sampling port 82. As well as facilitating application of the sample to the port, this avoids the need for a cutting operation to be carried out in the immediate vicinity of the inlet port 82, thereby reducing the likelihood of the capillary 65 becoming blocked by debris arising from the trimming operation.

Figure 9:
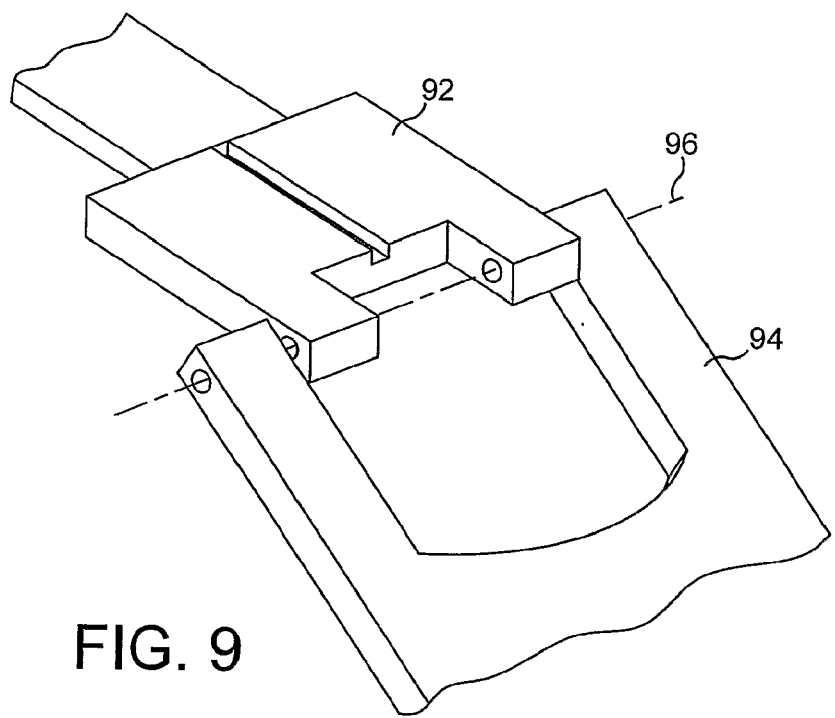
FIG. 9 shows another hinge arrangement for use with the invention.

While the thus described embodiments have been in one-piece form with integral hinge, this is not essential to the invention in its broadest concept. As can be seen in FIG. 9 the handle portion may alternatively be provided as a discrete item 94 which is pivotally hinged to the main body 92 of the test device via a hinge arrangement at a hinge axis 96, the bendable portion being constituted by the hinge arrangement. The hinge arrangement can include biasing means e.g. cooperating camming surfaces which preferentially cause the handle portion 94 to lie essentially in the plain of the body portion 92 while allowing the handle to be resiliently deflected as shown in FIG. 9 so as to allow access to the sampling port in the manner described in connection with the other embodiments previously described. The construction of such suitable camming surfaces is well known to those skilled in the art and will not be described further.

While dimensions have been given for the purpose of illustration, it will be appreciated that the invention in its broadest aspect is not limited thereto and that the configuration will need to reflect the requirements of the reader with which embodiments of the invention are to be used. Likewise the number of chambers may be greater or fewer than 2.

The invention claimed is:

1. A method of analyzing a sample comprising a test reader and a test device, said test device including an insertion portion and a handle portion, the method comprising the steps of:
    inserting the insertion portion of the test device into a test reader to connect the test device to the test reader,
    holding the handle portion of the device, which is hingedly attached to the insertion portion;
    deflecting the handle portion to reveal a sample application zone, which is located between the insertion and handle portions of the device;
    contacting blood to the sample application zone after inserting the insertion portion into the test reader; and
    removing the device from the test reader by manipulating the handle portion of the device.

2. The method of claim 1, wherein applying the sample comprises contacting blood present on a digit of a hand of a human to the sample application zone.

3. The method of claim 1, wherein the manipulating is performed by contacting the second portion of the device with at least first and second digits of a hand of a human.

4. The method of claim 3, wherein a distance between the sample application zone and an opposite terminal end of the second portion of the device is sufficient that the manipulating can be performed without the first and second digits contacting sample present at the sample input.

5. The method of claim 1, wherein a distance between the sample application zone and an opposite terminal end of the handle portion of the device is at least about 1 cm.

6. The method of claim 5, wherein the distance is at least about 1.5 cm.

7. The method of claim 5, wherein the handle portion of the device comprises at least one manipulatable surface having an area of at least about 0.6 $cm^2$.

8. The method of claim 7, wherein the surface has an area of at least about 1 $cm^2$.

9. The method of claim 7, wherein the surface has an area of at least about 1.25 $cm^2$.

10. The method of claim 1, wherein the deflecting is performed while at least some of the insertion portion of the first portion remains inserted in the test reader.

11. The method of claim 10, wherein the deflecting comprises doing so while at least about 75% of an inserted length of the insertion portion remains inserted in the test reader.

12. The method of claim 10, wherein deflecting comprises doing so before removing more than about 5% of the inserted length of the insertion portion.

13. The method of claim 1, wherein the angle is at least about 15 degrees.

14. The method of claim 1, wherein the angle is at least about 30 degrees.

15. The method of claim 1, wherein the deflecting is performed by contacting the handle portion of the device with at least first and second digits of a hand of a human.

16. The method of claim 1, wherein the deflecting is about an axis (a) extending generally perpendicular to a major axis of the device and (b) generally aligned with or adjacent to the sample application zone of the device.

* * * * *